US010562645B2

(12) United States Patent
Svanebjerg et al.

(10) Patent No.: US 10,562,645 B2
(45) Date of Patent: Feb. 18, 2020

(54) METHOD OF SAMPLING DE-ICING FLUID AND SYSTEM FOR SAMPLING DE-ICING FLUID

(71) Applicant: VESTERGAARD COMPANY A/S, Roskilde (DK)

(72) Inventors: Elo Svanebjerg, Tappernøje (DK); Stefan Vestergaard, Vanløse (DK)

(73) Assignee: VESTERGAARD COMPANY A/S, Roskilde (DK)

( * ) Notice: Subject to any disclaimer, the term of this patent is extended or adjusted under 35 U.S.C. 154(b) by 284 days.

(21) Appl. No.: 15/519,384

(22) PCT Filed: Oct. 24, 2014

(86) PCT No.: PCT/IB2014/065579
§ 371 (c)(1),
(2) Date: Apr. 14, 2017

(87) PCT Pub. No.: WO2016/063112
PCT Pub. Date: Apr. 28, 2016

(65) Prior Publication Data
US 2017/0233106 A1    Aug. 17, 2017

(51) Int. Cl.
B64F 5/23      (2017.01)
G01N 1/20      (2006.01)

(52) U.S. Cl.
CPC ............ B64F 5/23 (2017.01); G01N 1/2035 (2013.01); G01N 2001/205 (2013.01)

(58) Field of Classification Search
CPC  B64F 5/23; B64F 5/20; G01N 1/2035; G01N 2001/205

USPC ......................................................... 244/134
See application file for complete search history.

(56) References Cited

U.S. PATENT DOCUMENTS

| 4,275,593 A | 6/1981 | Thornton-Trump |
| 5,104,068 A * | 4/1992 | Krilla ................. B64F 5/20 |
| | | 134/123 |
| 2003/0127154 A1 | 7/2003 | Kneringer et al. |

FOREIGN PATENT DOCUMENTS

| CA | 2734001 A1 | 9/2011 |
| WO | WO 2006/121789 A2 | 11/2006 |
| WO | WO 2009/023342 A2 | 2/2009 |
| WO | WO 2011/113142 A1 | 9/2011 |
| WO | WO 2012/087235 A1 | 6/2012 |

* cited by examiner

Primary Examiner — Claude J Brown
(74) Attorney, Agent, or Firm — Birch, Stewart, Kolasch & Birch, LLP

(57) ABSTRACT

The invention provides a method of sampling de-icing fluid from an airplane de-icer having a spraying nozzle for spraying the de-icing fluid onto a surface of an airplane, the de-icing fluid preferably being produced by the airplane de-icer by mixing a number of ingredients. The method comprises the steps of: i) obtaining a limited sample of the de-icing fluid by diverting at least a part of the de-icing fluid flowing towards the spraying nozzle for a period of time during the spraying of the de-icing fluid onto the surface of the airplane, and ii) collecting sample of the de-icing fluid in a sample container. A system for sampling de-icing fluid is also provided as well as an airplane de-icer comprising the system.

22 Claims, 3 Drawing Sheets

METHOD OF SAMPLING DE-ICING FLUID AND SYSTEM FOR SAMPLING DE-ICING FLUID

Figure 1:
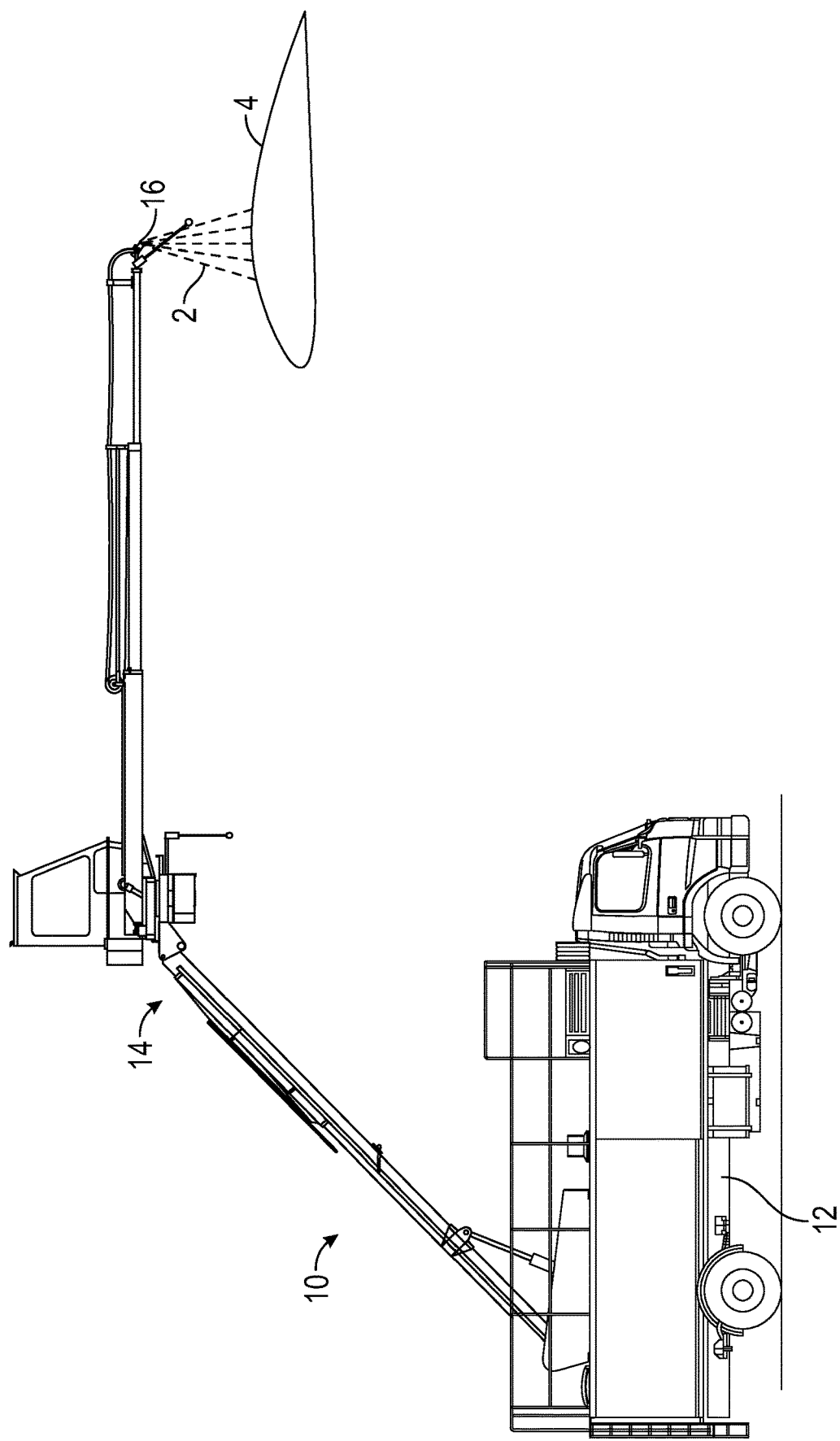

The present invention concerns a method of sampling de-icing fluid and a system for sampling de-icing fluid.

Traditionally, removal of ice from airplanes is done in two main steps, the first step being a de-icing step, wherein ice and snow deposited on the surface of the airplane is removed, the second step being an anti-icing step, wherein the surface of the airplane is covered with a protective fluid, which precludes formation of new ice on the surface of the airplane.

In the de-icing step it is known to use a pre-heated fluid, which is a mixture of water and a so called Type 1 de-icing fluid. The Type 1 de-icing fluid has a low viscosity and it is primarily the thermal energy of the fluid which causes the melting and removal of the ice (and possible snow deposits) from the airplane.

Typically, a Type 1 fluid is a pre-mixed fluid having propylene or ethylene glycol as the main constituents. In addition to this a typical Type 1 fluid comprises a number of so-called additives. These additives can for example be agents, which raise the flash point, or which reduce the tendency of formation of foam, or which are anti corrosive, or a mixture of all these, or other, agents.

The Type 1 fluid can be applied to a surface of an airplane in undiluted form, in which form it has the lowest freezing point, or it can be delivered in a premix of for example 50% or 75% Type 1 fluid mixed with water. It is customary to use these mixtures at higher temperatures, where a higher freezing point of the de-icing fluid can be allowed. A typical Type 1 fluid is constituted by 88% propylene or ethylene glycol, 10% water and 2% additives.

The anti-icing step is performed by applying a protective layer of anti-icing fluid on the surface of an airplane in order to prevent the formation of a new layer of ice on the surface of the airplane before it has left the runway.

The fluid, which is used for anti-icing is a fluid with a rather high viscosity (around 20.000 cSt. to around 30.000 cSt.). The high viscosity of the anti-icing fluid is achieved by adding polymers, which form long molecular strings in the anti-icing fluid. These molecular strings are rather sensitive to mechanical influence from the nozzle through which the anti-icing fluid is sprayed onto the outer surface of the airplane. This is due to the fact that these molecular strings can be broken into smaller pieces in the nozzle. Therefore, the anti-icing fluid is sprayed onto the outer surface of an airplane with a rather low and controlled pressure gradient (pressure drop) through the nozzle, whereby too big a mechanical influence is avoided. It is furthermore desirable to apply a uniform rather thin layer of the anti-icing fluid to the outer surface of the airplane. Hence, the anti-icing fluid is also sprayed onto said surface at a rather low flow rate, e.g. around 100 l/min.

The anti-icing fluid is called a Type 2 or Type 4 fluid, where the Type 4 fluid has a higher viscosity than the Type 2 fluid. A typical Type 2 or Type 4 fluid consists of 50% propylene or ethylene glycol, 48% water and 2% polymers and additives.

De-icing and anti-icing fluids are traditionally supplied to the airports or service companies, which perform de- and anti-icing for the airports, as Type 1, Type 2 or Type 4 fluids, which airports or service companies need to build up large stocks of these fluids before the onset of winter. Moreover, since these fluids are produced by relatively few producers in the world, it is often necessary to build up a rather large stock of these fluids in order to secure enough supplies to last a whole winter season. Furthermore, the scarcity of producers of these fluids also means that acquisition of these fluids incur rather big transport expenses in addition to the environmental problems related to the transportation of these fluids around the world. A wrong estimate of how long or hard a winter season will be may thus lead to a situation, where the airports and/or before mentioned service providers may run out of de- and anti-icing fluids.

An earlier patent application, WO2013/075731, by the present applicant provides a solution to the above mentioned disadvantages by proposing an airplane de-icer comprising a self-propelled vehicle provided with a lifting device for lifting and positioning a spraying nozzle in the vicinity of an outer surface of an airplane to be de-iced, the nozzle being fluidly connected to a tank assembly via at least one pipe, wherein the tank assembly comprises separate tanks for an anti-freeze fluid, such as propylene or ethylene glycol, additives, and water, each tank of the tank assembly being fluidly connected to a mixing system via pipes, the mixing system being configured for mixing the fluids from each of the tanks before supplying the mixed fluid to the nozzle.

As the de-icing of airplanes is essential to safety, it is necessary to ensure that the de-icing fluid actually applied to the airplanes is of the correct composition to ensure inter alia the correct freezing point and anti-icing properties. Traditionally samples have been taken on the de-icing fluids as they are delivered by the producers to the service companies. Fluid samples may also be taken by directly from the fluid sprayed out by the airplane de-icer, indeed, where the air-plane de-icer is of the type encompassed by WO2013/075731, this latter type of sampling is the only one hitherto available as the de-icing fluid is produced, by mixing of the constituents, in the airplane de-icer itself.

This type of sampling, i.e. by spraying de-icing fluid from the airplane de-icer, is however highly wasteful money-wise, and detrimental to the environment as large quantities, such as 25-30 litres, of the de-icing fluid must be sprayed from the nozzle of the airplane de-icer in order to ensure that the de-icing fluid sampled is representative of the de-icing fluid used during the subsequent de-icing of an airplane and not affected by the de-icing/anti-icing fluid stagnating in the conduits, pumps and mixing devices of the airplane de-icer.

Furthermore, this type of sampling generally disturbs the normal use of the airplane de-icer by taking up time that could be used to de-ice airplanes.

It is therefore an object of the present invention to provide a method of sampling de-icing fluid which is less wasteful.

It is further an object of the present invention to provide a method of sampling de-icing fluid where a sample is taken during de-icing of an airplane.

It is furthermore an object of the present invention to provide a system for carrying out the method.

At least one of the above objects, or at least one of the further objects which will be evident from the below description of the present invention, is according to the first and second corresponding aspects of the present invention achieved by a method of sampling de-icing fluid as defined in claim 1 and a system for carrying out the method as defined in claim 7.

By diverting at least a part of the de-icing fluid flowing towards the nozzle for a period of time during the spraying of the de-icing fluid onto the surface of the airplane, the sampling of de-icing fluid may be performed during de-icing of the airplane. This saves time and waste as a separate spraying for obtaining a sample in the conventional way, is not needed. Furthermore, as the sample is taken from de-icing fluid which has not yet reached the spraying nozzle, less de-icing fluid needs to be sprayed before the collected sample of de-icing fluid is representative of the de-icing fluid that is sprayed.

The Obtaining of the Limited Sample is Preferably Performed Using a Valve

In the context of the present invention the term "limited sample" encompasses "a delimited sample", in other words a sample being collected during a period of time and having a desired volume so that the sample can be stored for analysis outside said period of time. In particular is the term limited sample to be understood as not covering a continuous sample, i.e. where fluid to be sampled continuously passes through a sample container or measurement cell.

In the context of the present invention, de-icing fluid is to be understood as also comprising de-icing fluid, anti-icing fluid, or both. The de-icing fluid may be carried by the airplane de-icer or alternatively be produced by the airplane de-icer by mixing a number of ingredients.

Preferably only a part of the de-icing fluid is diverted, however it is also contemplated within the context of the present invention that all of the de-icing fluid is diverted, leading to very short interruption in the spraying of the de-icing fluid onto the surface of the airplane, during which interruption the de-icing fluid instead quickly fills the sample container for providing the sample.

The de-icing fluid is diverted at a position in which the de-icing fluid flows towards the spraying nozzle. This corresponds to a position upstream of the spraying nozzle. This position may for example be between a tank of the de-icing fluid and a pump pumping the de-icing fluid, or between a pump pumping the de-icing fluid and the spraying nozzle, i.e. in a supply line or pipe leading to the spraying nozzle. Where the airplane de-icer produces the de-icing fluid by mixing a number of ingredients, this position should be downstream of the position where all of the number of ingredients has been mixed but upstream of the spraying nozzle.

The period of time depends on the volume of the sample container and the flow rate of the de-icing fluid towards the spraying nozzle. The duration of time may for example be from 1-60 seconds.

In the context of the present invention the expression "during the spraying of said de-icing fluid onto said surface of said airplane" encompasses the expression "during the spraying of said de-icing fluid from said spraying nozzle" and the expression "during the flowing of said de-icing fluid towards said spraying nozzle".

The surface of the airplane may for example be a wing or a part of the surface of a wing.

In the context of the present invention term "collecting" encompasses receiving and/or storing.

The sample container may for example have a volume of 0.05 litres to 1 litre such as 0.2 to 0.5 litres. The sample container may for example be made of plastic such as PET plastic. Alternatively the sample container may be made of metal.

The valve may be a slide valve. The valve may be fluidly connectable to the supply line or pipe by being fluidly connected to an aperture in the wall of the supply line or pipe, by being fluidly connected to a side branch of the supply line or pipe, or by being connected to a manifold to which the supply line or pipe is connected or passes through. In either case, the valve may have a first closed state in which no de-icing fluid can pass through the valve to be collected in the sample container and a second, open, state in which de-icing fluid can flow through the valve to be collected in the sample container. The valve can be actuable by comprising a valve element, affectable from outside the valve and moveable between a first position in which the valve element prevents flow of de-icing fluid through the valve, corresponding to the first closed state, and a second position, in which the valve element no longer prevents flow of de-icing fluid through the valve, corresponding to the second open state.

The sample container is typically fluidly connected to the valve via a pipe or tube. A further valve may be provided between the valve and the sample container, this further valve being connected to a drain tank for draining the pipe or tube between the valve and the sample container between collecting samples for preventing contamination of a subsequent sample by a previous sample.

The sample container should be at least partly filled. Preferably the sample container is fully filled to reduce any headspace in the sample container and thereby reducing any changes in sample composition due to evaporation of the sample of de-icing fluid.

The sample in the sample container may be analysed by using a hand instrument such as a refractometer, this analysis for example being performed by an operator of the airplane de-icer. Preferably, however, and in order to ensure the highest safety, traceability and authority, the sample is analysed by a laboratory which may be remote from the airplane de-icer and independent from the airport, the service company, and the operator of the airplane de-icer. This is especially important where the de-icing fluid is produced in the airplane de-icer as in this case the composition of the de-icing fluid is determined by the quality of the ingredients and the way the ingredients are mixed in the airplane de-icer. The analysis may for example determine the contents such as the concentration of anti-freeze fluid, such as propylene or ethylene glycol, additives, and water. Further the analysis may comprise determining the de-icing properties, such as freezing point and viscosity, of the de-icing fluid.

The system according to the second aspect of the present invention is suitable for performing the method according to the first aspect of the present invention.

Claim 8 defines a preferred embodiment of the system according to the second aspect of the present invention. Although the sampling of de-icing fluid may be performed manually, for example by manually actuating the valve by rotating a knob or lever affecting the valve element and keeping the valve in the second open state for the period of time, it is preferred to use the sampling control device, which for example may comprise a micro-computer, integrated circuit, or other computer, as this provides reproducible sampling and allows for automating the sampling of the de-icing fluid.

The valve actuation device may for example comprise an electric servo motor for affecting the valve element. Alternatively the valve actuation device may comprise a hydraulic or pneumatic cylinder and piston unit for affecting the valve element. In the first case the sampling control device may energize the servo motor directly. In the second case the sampling control device may energise a magnetic valve for causing hydraulic fluid or pressurized air to flow into or out of said cylinder and piston unit for affecting the valve member.

Furthermore the valve may be a magnetic valve in which case the valve actuation device is the spool which when energized by the sampling control device affects the valve member. The sampling control device may comprise a clock and may be configured, for example by a computer program, to actuate the valve for the period of time as determined by the clock.

It is further contemplated with the context of the present invention that the sampling control device may comprise a mechanical or electrical device such as a mechanical or electrical timer or a clockwork motor configured for actuating the valve for the period of time.

The preferred embodiments of the method and system according to the corresponding first and second aspects of the present invention defined in claims 2 and 9 are advantageous in that they make it easy to analyze the sample of de-icing fluid at a laboratory remote from the airplane de-icer. Furthermore these embodiments make it possible to exchange a sample container which has collected a sample with an empty, i.e. not containing a sample, sample container. Typically a sample container is removed from the system and/or the airplane de-icer once it has collected the sample. The sample container with the sample of the de-icing fluid may then be stored for being analysed at a later time, or not analysed at all, if desired. The latter situation may for example be the case where a first sample of de-icing fluid was collected during the de-icing of a first airplane, which first airplane is then delayed with the result that it must be de-iced again. In this case there is no point in analysing the first sample as it would be better to collect a second sample during the second de-icing of the first airplane. The sample of de-icing fluid is analysed as described above.

The sample of de-icing fluid may be obtained at numerous different points in time or in relation to numerous different events as defined in the embodiments of the method and system according to the corresponding first and second aspects of the present invention as defined in claims 3 and 10.

Thus the method according to the first aspect of the present invention may comprise determining an amount of de-icing fluid having been sprayed by the spraying nozzle, and comparing this amount to a predetermined amount to determine when a sample of the de-icing fluid is to be obtained. This may be implemented in the system according to the second aspect of the present invention by providing a flow measurement device in the supply line or pipe leading to the spraying nozzle, or alternatively providing a sensor for determining the rotational speed of a pump pumping de-icing fluid or an ingredient of a de-icing fluid and using the rotational speed to determine the amount, while the sampling control device is configured to compare the amount of de-icing fluid thus determined with a stored amount and based on this comparison actuating the valve actuation device.

The system may also comprise a sensor such as a level sensor for sensing the level of an ingredient in a tank for one of the ingredients for producing the de-icing fluid, the sensor reporting a value to the sampling control device which is configured to compare this value to a previous value and from this comparison determining whether the tank has been replenished and whether the valve actuation device should be actuated for collecting a sample of said de-icing fluid. The sampling control device may, as described above, comprise a clock and the sampling control device may further comprise a counter for counting each use of the airplane de-icer, the sampling control device being configured, by programming, to actuate the valve actuation device when the counter and the clock indicate that it is the first de-icing of the day. The sampling control device may further be configured, by programming, to actuate the valve actuation device at set values reported by the clock or the counter, the set values corresponding to a sampling schedule, such as every day, every second day, every second use of the airplane de-icer etc.

Further the system may comprise an input device, useable by an operator of the airplane de-icer and connected to the sampling control device for instructing the sampling control device, by being used to input and record a command which is then compared to a stored command in the sampling control device, to actuate the valve actuation device for obtaining the sample of the de-icing fluid. The input device, or the sampling control device, can get a signal to take a sample from a coordinator in the airport via a data transmission system, connecting the airplane de-icer with the coordinator in the airport.

In the above cases, the obtaining of a sample requires that de-icing fluid is actually flowing towards the spraying nozzle such as during spraying of the de-icing fluid onto the surface of the aircraft. Accordingly, the method and system may comprise determining, by using a flow sensor or a sensor for determining the rotational speed of a pump, whether de-icing fluid is actually flowing towards the spraying nozzle, i.e. whether the airplane de-icer is used, and only actuating the valve actuating device when this is the case.

The coordinator system may be operated by a coordinator or may alternatively or additionally comprise a clock and a sampling schedule. The airport is the airport in which the airplane de-icer operates for de-icing airplanes starting from the airport. The data transmission system may comprise a radio link such as a wireless data network such as a WIFI, a mobile network such as GSM, 3G, 4G, 5G etc. The signal to take a sample may for example comprise an SMS, an email, or a computer command sent to the airplane de-icer. The sampling control device of each airplane de-icer operating at the airport may for example have its own user identity for logging into the coordinator system and for polling the coordinator system for retrieving any pending requests for taking samples for the specific airplane de-icer. Alternatively each airplane de-icer or sampling control device comprises or is connected to a mobile phone for receiving the SMS and for extracting a signal for taking a sample from the SMS.

The preferred embodiment of the system according to the second aspect of the present invention as defined in claim 11 is advantageous as it prevents or at least lessens the risk and occurrences of the sample of de-icing deteriorating during storing, e.g. due to heat if stored indoors, or due to the sun's radiation. Correspondingly, the method according to the first aspect of the present invention may comprise the step of insulating and/or shielding the sample of de-icing fluid from the sun's radiation.

The preferred embodiment of the system according to the second aspect of the present invention as defined in claim 12 is advantageous as it prevents or at least lessens the risk of tampering with the sample of de-icing fluid. The breakable seal provides an easy way of accessing the sample, e.g. by a laboratory performing the analysis of the sample, and also functions as an indication of tampering, i.e. if the seal is damaged or ruptured when received by the laboratory. The sample container may further comprise a second one-way valve for allowing air to escape from the interior of the sample container during the collecting of the sample of de-icing fluid. The one-way valve may comprise a fitting such as a screw fitting or bayonet coupling for fluidly connecting the sample container to a corresponding fitting on a pipe or tube of the system. The screw fitting or bayonet coupling, and the corresponding fitting may be configured for connection only such that the removal of the sample container from the fitting causes the destruction of the screw fitting or bayonet coupling so that the sample container, after disconnection from the fitting, can no longer be reattached.

The preferred embodiment of the system according to the second aspect of the present invention as defined in claim 13 is advantageous as it reduces the need for multiple sample containers in cases where not every sample of de-icing fluid must be stored for analysis, instead the same sample container may be used to collect a new sample of de-icing fluid. The drain valve may for example be placed in the bottom of the sample container. The system may comprise a drain valve actuation device controllable by the sampling control device for actuating the drain valve if the sampling control device, by being so configured by programming or upon an instruction from the operator of the airplane de-icer via an input device, determines that the drain valve should be actuated. Correspondingly, the method according to the first aspect of the present invention may comprise the step of draining the sample container for receiving a new or further sample of de-icing fluid.

Preferably the system comprises a drain tank for receiving said sample if said sample is drained from said sample container. The drain valve may also be used to drain all or part of the sample into a bottle or suitable test tube for analyzing the sample.

Preferably, as per claim 4 defining a preferred embodiment of the method according to the second aspect of the present invention, a plurality of samples are collected by a plurality of sample containers thus allowing the airplane de-icer to operate at a high safety level by allowing analysis the plurality of samples, such as for example on sample for each airplane de-iced by the airplane de-icer.

Claims 4 and 14 define preferred embodiments of the method and system according to the corresponding first and second aspects of the present invention. Using a sample container magazine makes it simpler to handle and keep track of a plurality of sample containers. The sample container magazine may comprise a structure, such as a frame, matrix or cassette for holding and positioning individual sample containers, or alternatively the sample containers may be formed integrally with the sample container magazine. The sample container magazine may for example be configured as a revolving magazine with sample containers placed in a circle, or alternatively as a translating magazine with sample containers placed in a line or array. In the former case, the sample containers in the sample container magazine may be provided with drain valves and the system further comprises a structure to actuate the drain valve of the sample container positioned in the position prior to the position in which the sample container can collect the sample of de-icing fluid. Such a sample container magazine would be advantageous as it would continuously keep for example the last 12 samples stored, corresponding to in total 12 sample containers in the sample container magazine, while continuously reusing, by draining, the sample container containing the oldest sample. This is advantageous where an analysis of the samples of de-icing fluid is only infrequently required as it decreases the need for replacing the sample container magazine.

Alternatively, where the sample containers in the sample container magazine are not reused as described above the whole sample container magazine is simply removed, and exchanged for a sample container magazine with empty sample container once all sample containers have collected a sample of de-icing fluid.

The sample container magazine advancement device typically comprises an electric motor or electrically driven ratchet and pawl mechanism for step-wise advancement of the sample container magazine. Preferably the sample container connected to the valve is changed in steps. Alternatively the sample container magazine advancement device may comprise a mechanical ratchet and pawl mechanism, a rotating spindle carrying the sample container magazine and driven by a manually rotatable knob, or a hydraulic or pneumatically driven turbine or piston and cylinder unit.

The sample container magazine may comprise a position data carrier for storing information about which of the sample container in the sample container magazine has been used. The position data carrier may for example be accessed and written by the sampling control device, or alternatively the sample container magazine comprises sensors for sensing when a sample container collects a sample and recording this information in the position data carrier. The position data carrier may for example be used to prevent re-use of the sample container magazine once all sample containers, i.e. all positions, have been used. The sample container magazine may further comprise a tampering sensor for detecting attempts at tampering with the sample container magazine and for storing information about these attempts in the position data carrier or in another data carrier provided in the sample container magazine.

Preferably, as per the preferred embodiment of the system according to the second aspect of the present invention as defined in claim 15 the sampling control device is configured for causing the sample container magazine advancement device to change which of the plurality of sample containers is fluidly connected to the valve at said one time. Preferably the sampling control device is connected electrically to the sample container magazine advancement device, however, it is further contemplated that if the sampling control device comprises a mechanical or electrical device such as a mechanical or electrical timer or a clockwork motor configured for actuating the valve for the period of time, the sample container magazine advancement device may comprise a mechanical rack and pawl mechanism driven by the timer or the clockwork motor.

The sample container may be fluidly connected to the valve by being placed under the open end of a pipe or tube running from the valve to the sample container.

The embodiments of the method and system according to the corresponding first and second aspects of the present invention as defined in claims 6 and 16 are advantageous as they increase the safety and traceability of the de-icing of airplanes. A further advantage is that the information, when evaluated together with the analysis of the sample, may be used to find faults in the operation of the airplane de-icer, in particular where the de-icing fluid is produced in the airplane de-icer from a number of ingredients.

The information may be any information relating to the circumstances of obtaining the sample, some examples being the ambient temperature at the time of obtaining the sample and/or at specific time prior to obtaining the sample, the current time, the type of airplane de-icer from which the sample is collected, the flow rate of de-icing fluid during collecting the sample, the GPS position of the air-plane de-icer, an identification of the airplane being de-iced, an identification of the operator of the airplane de-icer etc.

The information device may thus for example be a temperature sensor, a clock, an information carrier storing the type of airplane de-icer, a flow rate sensor, a GPS device, a camera for photographing the airplane being de-iced, an input device for receiving an identification of the airplane being de-iced or an information carrier comprising this information, an input device for registering the name of the operator of the airplane de-icer or alternatively a smart card reader or finger print sensor for registering the identity of the operator, etc.

The information may be stored in an information carrier or memory in the airplane de-icer, but is preferably stored in an information carrier or memory in the sample container or the sample container magazine. Alternatively, the information may be uploaded wirelessly to an information storage such as a server on the internet or the coordinator system at the airport.

At least one of the above objects, or at least one of the further objects which will be evident from the below description of the present invention, is according to a third aspect of the present invention achieved by an airplane de-icer comprising a system according to the second aspect of the present invention achieved as defined in claim 17.

Preferably the airplane de-icer comprises a self-propelled vehicle provided with a lifting device for lifting and positioning a spraying nozzle in the vicinity of an outer surface of an airplane to be de-iced, said spraying nozzle being fluidly connected to a tank assembly via at least one pipe. A pump may be provided for pumping the de-icing fluid to the spraying nozzle.

The embodiment of the airplane de-icer according to the third aspect of the present invention as defined in claim 18 is advantageous as it provides an airplane de-icer capable of producing the de-icing fluid from a number of ingredients while allowing samples of the produced de-icing fluid to be taken. The additives may for example contain additives for increasing the viscosity of the de-icing fluid.

Figure 2:
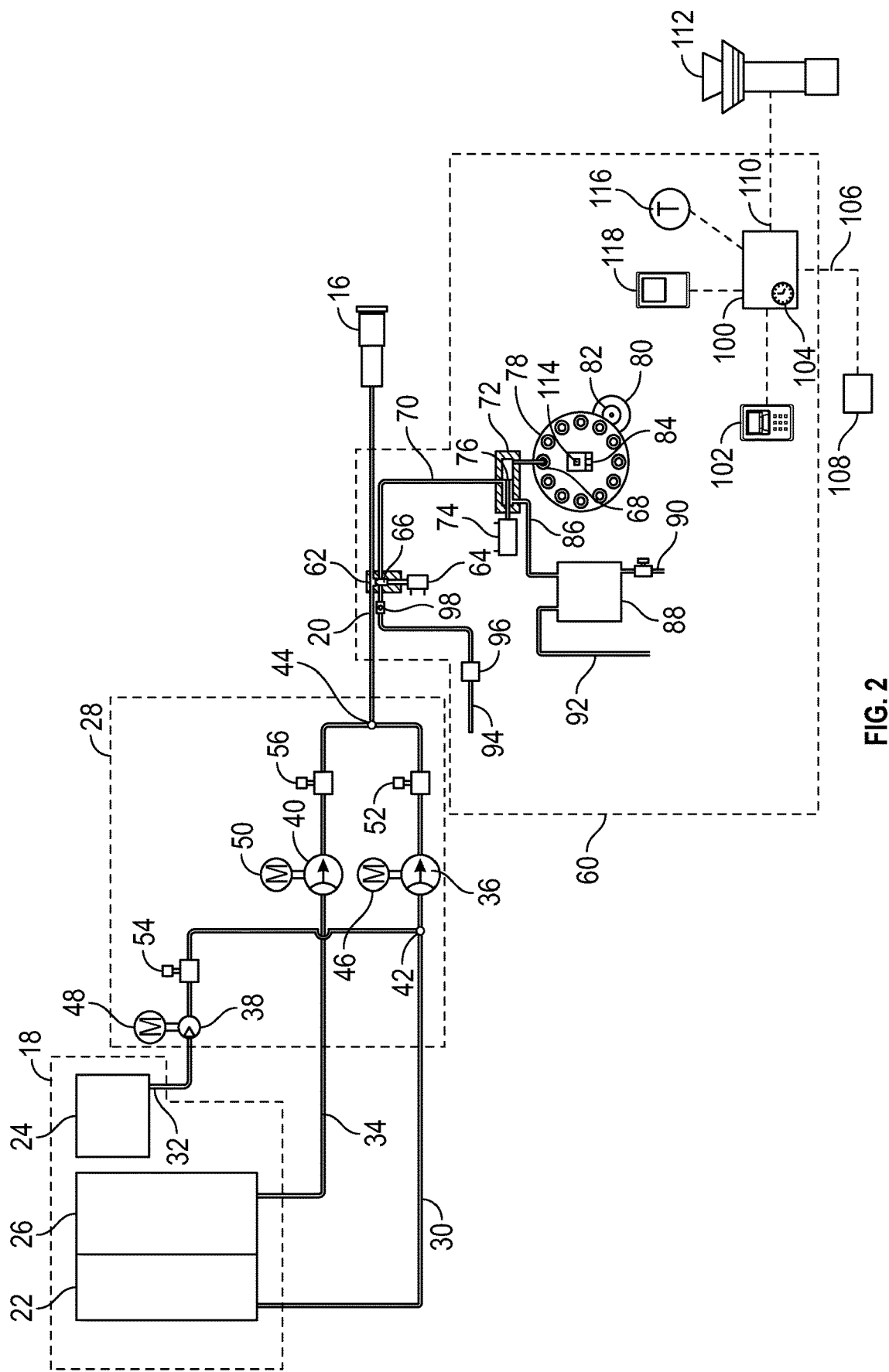
Figure 3:
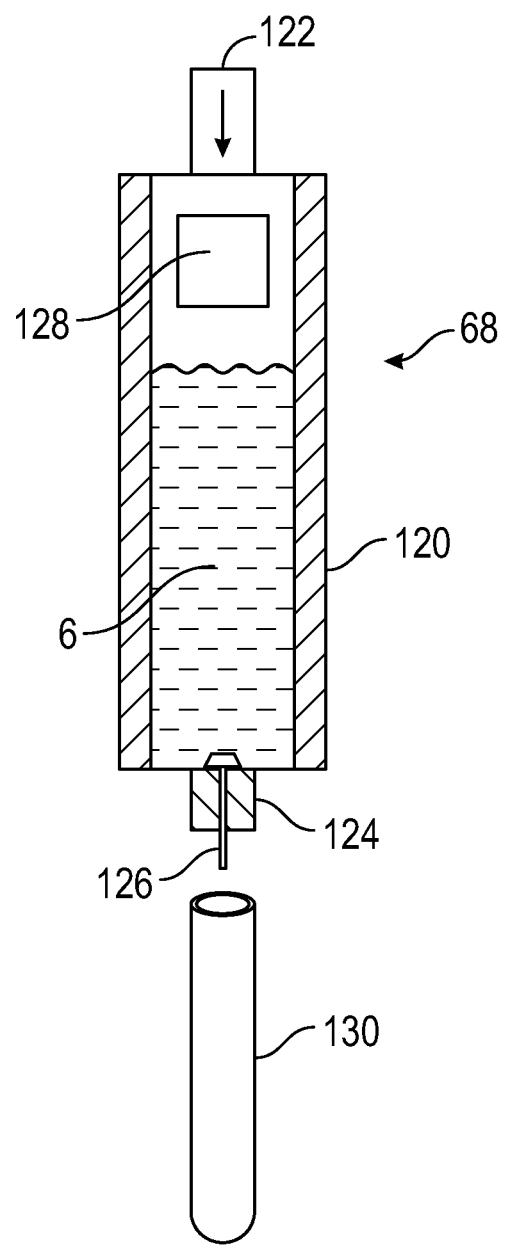

The invention and its many advantages will be described in more detail below with reference to the accompanying schematic drawings, which for the purpose of illustration show some non-limiting embodiments, and in which:

FIG. 1 shows an embodiment of an airplane de-icer according to the third aspect of the present invention comprising a system according to the second aspect of the present invention, FIG. 2 shows the liquid delivery system of the first embodiment of the airplane de-icer and an embodiment of a system according to the second aspect of the present invention, and, FIG. 3 shows an embodiment of a sample container.

In the below description, one or more 'signs added to a reference number indicate that the element referred to has the same or similar function as the element designated the reference number without the 'sign, however, differing in structure.

Additionally, where useful for discussing two or more identical elements, a subscript Arabic numeral is used to designate such further identical elements.

When further embodiments of the invention are shown in the figures, the elements which are new, in relation to earlier shown embodiments, have new reference numbers, while elements previously shown are referenced as stated above. Elements which are identical in the different embodiments have been given the same reference numerals and no further explanations of these elements will be given.

FIG. 1 shows an airplane de-icer 10 comprising a self-propelled vehicle 12 and provided with a lifting device 14 for lifting and positioning a spraying nozzle 16, the spraying nozzle 16 spraying a de-icing fluid 2 onto an outer surface 4 of an airplane to be de-iced.

FIG. 2 shows the fluid delivery system of the airplane de-icer 10 where it can be seen that the spaying nozzle 16 is fluidly connected to a tank assembly 18 via a pipe 20. The tank assembly 18 comprises separate tanks 22, 24 and 26, respectively, for an anti-freeze fluid, such as propylene or ethylene glycol, additives, and water, each tank 22, 24, 26 of the tank assembly 18 being fluidly connected to a mixing system 28 via pipes 30, 32, and 34, respectively, the mixing system 28 comprising separate pumps 36, 38, and 40, respectively, for pumping the fluids from the respective three tanks 22, 24 and 26 to the mixing points 42 and 44, the mixing point 44 being the point where the fluid from all three tanks 22, 24 and 26 have been mixed into to produce the de-icing fluid. Control of the mixing is obtained by controlling the pumps 36, 38 and 40, which pumps are driven by the electric or hydraulic motors 46, 48 and 50, based on flow rate transmitters 52, 54 and 56 associated with the pumps 36, 38, and 40 and/or the pipes 30, 32 and 34 to ensure the correct ratio between the respective fluids from the three tanks 22, 24 and 26. The pipe 20 is fluidly connected to the mixing system 28 at mixing point 44 for receiving the de-icing fluid.

As can be seen from the above, the airplane de-icer 10 is of the type that produces the de-icing fluid in the airplane de-icer by mixing a number of ingredients, however, when now turning to describing the system 60 according to the second aspect of the present invention, it will be understood that the system 60 is useable for sampling de-icing fluid from an airplane de-icer having but a single tank and pump, the tank being filled with a ready-to-use de-icing fluid.

System 60 comprises a valve 62 fluidly connected to the pipe 20 and actuable by a valve actuation device represented by an actuator 64 connected to a moveable valve element 66 in the valve 62, the valve element 66 being moveable for selectively diverting a part of the de-icing fluid flowing through the pipe 20 into the system 60. The actuator 64 may be electromagnetic, hydraulic or pneumatic.

A sample container 68, shown in top view, is connected to the valve 62 via a pipe 70 and valve 72 for collecting a sample 6, shown in FIG. 3, of the de-icing fluid. Valve 72 is actuated by an actuator 74 moving a moveable valve element 76. The actuator 74 may be electromagnetic, hydraulic or pneumatic.

The sample container 68 is one of a plurality of sample containers held in sample container magazine 78 which is advanced by the stepwise rotating of the sample container magazine 78 by a motor 80 and wheel 82, the motor 80 and wheel 82 representing a sample container magazine advancement device. The sample container magazine 78 further comprises a data carrier 84 for storing information relating to the circumstances of the obtaining of a sample 6 in each and every of the sample containers 68.

The valve element 76 has two positions, one for leading a sample 6 of de-icing fluid to the sample container 68 and one for fluidly connecting the pipe 70 with a drain pipe 86 leading to a drain tank 88 having a drain valve 90 and an overflow pipe 92.

A flush-pipe 94 is connected via a flush buffer tank 96 and a one-way valve 98 to the valve 62.

Valves 62 and 72 have respective first states in which valve 62 connects flush-pipe 94 to the pipe 70 and in which pipe 70 is connected to pipe 86. In this position, air is drawn into the flush-pipe 94 and allows any de-icing fluid in the pipe 70 to be drained to the drain tank 88 for preventing cross contamination of samples.

Valves 62 and 72 have also respective second states in which valve 62 diverts de-icing fluid from the pipe 20 into the pipe 70 and in which valve 72 directs the de-icing fluid into the sample container 68.

Valves 62 and 72, through actuators 64 and 74, are controlled by sampling control device 100. Sampling control device 100 may for example be connected to an input device 102, for receiving manual input by an operator of the airplane de-icer 10 to obtain a sample 6. Sampling control device 100 may further comprise a clock 104 for obtaining samples 6 at specific time points. Further, sampling control device 100 may be configured for receiving measurements of flow rates from one or more of flow rate transmitters 52, 54 and 56 and to obtain a sample after a certain total volume of flow, as calculated using the flow rates during a set time specified by the clock 104. The measurements of flow rates from one or more of flow rate transmitters 52, 54 and 56 may be obtained directly from the flow rate transmitters 52, 54 and 56 by the sampling control device 100. Alternatively the measurements, as well as other signals relating to the operation of the airplane de-icer 10, may be received via a connection 106 to a control system 108 of the airplane de-icer 10. Furthermore the input device 102 or the sampling control device 100 can get a signal to take a sample 6 from a coordinator in the airport via a data transmission system 110 connecting the airplane de-icer 10 with a coordinator system 112 in the airport.

Information 114 relating to the circumstances of the obtaining of a sample 6 may be obtained from information devices such as a temperature sensor 116 and a GPS position sensor 118. The information is collected by the sampling control device 100 and stored in the information carrier 84 so that the information may be read when the sample of de-icing fluid in sample container 68 is analyzed by removing the sample container magazine 78 and transporting it to a laboratory.

FIG. 3 shows a side view of the sample container 68 which may comprise a plastic bottle surrounded by an opaque insulating jacket 120 for insulating the sample 6 of de-icing fluid and for protecting it against sun radiation. The sample container 68 may further comprise a one-way valve 122 for receiving and passing the sample 6 of de-icing fluid into the sample container 68. The bottom of the sample container 68 may provide a drain valve 124 having a valve element 126 which when pushed towards the bottom of the sample container allows the sample 6 of de-icing fluid to be drained from the sample container 68. A structure (not shown), such as a cam for engaging the valve element 126, may be positioned for draining the sample container in the position prior to the position of the sample container 68 in the sample container magazine in FIG. 2. As the sample container magazine is advanced by being rotated in the same direction the oldest sample 6 will automatically be drained and the sample container magazine will then always contain the last number of samples, corresponding to the number of sample containers 68 in the sample container magazine 78. The sample container 68 may further comprise a breakable seal 128 which can be broken to access the sample of de-icing fluid for analysis. The sample container 68 may also be drained into a test tube or bottle 130, for analyzing, using the drain valve 124.

LIST OF PARTS WITH REFERENCE TO THE FIGURES

| 2. | De-icing fluid |
|---|---|
| 4. | Surface of an airplane |
| 6. | Sample of de-icing fluid |
| 10. | Airplane de-icer |
| 12. | Self-propelled vehicle |
| 14. | Lifting device |
| 16. | Spraying nozzle |
| 18. | Tank assembly |
| 20. | Pipe |
| 22. | Tank (for antifreeze fluid) |
| 24. | Tank (for additives) |
| 26. | Tank (for water) |
| 28. | Mixing system |
| 30. | Pipe |
| 32. | Pipe |
| 34. | Pipe |
| 36. | Pump (for antifreeze fluid) |
| 38. | Pump (for additives) |
| 40. | Pump (for water) |
| 42. | Mixing point |
| 44. | Mixing point |
| 46. | Electric or hydraulic motor |
| 48. | Electric or hydraulic motor |
| 50. | Electric or hydraulic motor |
| 52. | Flow rate transmitter |
| 54. | Flow rate transmitter |
| 56. | Flow rate transmitter |
| 60. | System |
| 62. | Valve |
| 64. | Actuator for valve |
| 66. | Valve element |
| 68. | Sample container |
| 70. | Pipe |
| 72. | Valve |
| 74. | Actuator for valve |
| 76. | Valve element |
| 78. | Sample container magazine |
| 80. | Motor |
| 82. | Wheel |
| 84. | Information carrier |
| 86. | Drain pipe |
| 88. | Drain tank |
| 90. | Drain valve |
| 92. | Overflow pipe |
| 94. | Flush pipe |
| 96. | Flush buffer tank |
| 98. | One-way valve |
| 100. | Sampling control device |
| 102. | Input device |
| 104. | Clock |
| 106. | Connection to control system of the airplane de-icer |
| 108. | Control system of airplane de-icer |
| 110. | Data transmission system |
| 112. | Coordinator system |
| 114. | Information |
| 116. | Temperature sensor |
| 118. | GPS |
| 120. | Insulating jacket |
| 122. | One-way valve |
| 124. | Drain valve |
| 126. | Valve element |
| 128. | Breakable seal |
| 130. | Bottle or test tube |

The invention claimed is:

1. A method of sampling de-icing fluid from an airplane de-icer having a spraying nozzle for spraying said de-icing fluid onto a surface of an airplane, said de-icing fluid preferably being produced by said airplane de-icer by mixing a number of ingredients, the method comprising the steps of:

obtaining a limited sample of said de-icing fluid by actuating a valve and thereby diverting at least a part of said de-icing fluid flowing towards said spraying nozzle for a period of time during the spraying of said de-icing fluid onto said surface of said airplane, and collecting said sample of said de-icing fluid in a sample container.

2. The method according to claim 1 further comprising the steps of:
storing said sample in said sample container in said airplane de-icer, and, optionally
removing said sample container from said airplane de-icer before analysing said sample of said de-icing fluid.

3. The method according to claim 2 wherein said sample is obtained at a point in time corresponding to any of: when a first amount of de-icing fluid has been sprayed onto said surface of said airplane; when said airplane is the first airplane of the day onto which surface said de-icing fluid is sprayed; when one of said number of ingredients have been replenished; a time point in a sampling schedule; a time point selected by an operator of said airplane de-icer, a time point sent to said airplane de-icer from a coordinator system in an airport via a data transmission system.

4. The method according to claim 2 wherein said steps of obtaining said sample and collecting said sample are performed a plurality of times at different points in time for obtaining a plurality of samples, each sample being collected in a corresponding one of a plurality of sample containers.

5. The method according to claim 1 wherein said sample is obtained at a point in time corresponding to any of: when a first amount of de-icing fluid has been sprayed onto said surface of said airplane; when said airplane is the first airplane of the day onto which surface said de-icing fluid is sprayed; when one of said number of ingredients have been replenished; a time point in a sampling schedule; a time point selected by an operator of said airplane de-icer, a time point sent to said airplane de-icer from a coordinator system in an airport via a data transmission system.

6. The method according to claim 1 wherein said steps of obtaining said sample and collecting said sample are performed a plurality of times at different points in time for obtaining a plurality of samples, each sample being collected in a corresponding one of a plurality of sample containers.

7. The method according to claim 6, said plurality of sample containers being provided in a sample container magazine carried by said airplane de-icer, the method further comprising the steps of:
once said plurality of sample containers have collected said plurality of samples of de-icing fluid: exchanging said sample container magazine in said airplane de-icer with a further sample container magazine, the plurality of sample containers of said further sample container magazine being empty for collecting a plurality of samples of said de-icing fluid.

8. The method according to claim 1 further comprising the steps of:
obtaining information relating to the circumstances of obtaining said sample of said de-icing fluid, and
storing said information in said airplane de-icer, and/or in an information carrier comprised by said sample container, and/or in an information storage, such as said coordinator system, separate from said airplane de-icer and said sample container.

9. A system for sampling de-icing fluid comprising
a valve fluidly connectable to a supply line or pipe leading de-icing fluid towards a spraying nozzle of an airplane de-icer, said valve being actuable for obtaining a limited sample of said de-icing fluid by diverting at least a part of said de-icing fluid flowing through said supply line or pipe towards said spraying nozzle for a period of time during the spraying of said de-icing fluid onto said surface of said airplane,
a sample container fluidly connected to said valve for receiving said sample of said de-icing fluid and for being at least partly filled by said sample of de-icing fluid, and
a valve actuation device connected to said valve for actuating said valve.

10. The system according to claim 9 further comprising
a sampling control device connected to said valve actuation device for causing said valve actuation device to actuate said valve, said sampling control device further being configured for causing said valve actuation device to actuate said valve for said period of time.

11. The system according to claim 10, said sampling control device being configured to obtain said sample at a point in time corresponding to any of: when a first amount of de-icing fluid has been sprayed onto said surface of said airplane; when said airplane is the first airplane of the day onto which surface said de-icing fluid is sprayed; when one of said number of ingredients have been replenished; a time point in a sampling schedule; a time point selected by an operator of said airplane de-icer, a time point sent to said airplane de-icer from a coordinator system in an airport via a data transmission system.

12. The system according to claim 9, said sample container being removable from said system for analyzing, at a location remote from said system, all or part of said sample of said de-icing fluid in said sample container for determining the contents and/or de-icing properties of said sample of said de-icing fluid.

13. The system according to claim 9, said sample container being insulated and/or opaque.

14. The system according to claim 9, said sample container comprising a one-way valve connected for receiving said sample of de-icing fluid and for leading said sample of de-icing fluid into said sample container.

15. The system according to claim 14, said sample container further comprising a breakable seal for providing access to said sample of de-icing fluid for analysing said sample of de-icing fluid.

16. The system according to claim 9, said sample container comprising a drain valve for allowing said sample of said de-icing fluid to be drained from said sample container into a bottle or suitable test tube for analyzing said sample, or alternatively into a drain tank if said sample is not to be analysed.

17. The system according to claim 9, said system further comprising a sample container magazine comprising a plurality of said sample containers of which at one time only one of said sample containers are fluidly connected to said valve, said sample container magazine preferably being removable from said system for exchanging said sample container magazine in said airplane de-icer and/or said system with a further sample container magazine, the plurality of sample containers of said further sample container magazine being empty for collecting a plurality of samples of said de-icing fluid, and a sample container magazine advancement device for changing which one of said plurality of sample containers is fluidly connected to said valve at said one time.

18. The system according to claim 17, said sampling control device being:
connected to said sample container magazine advancement device for causing the changing of which one of said plurality of sample containers is fluidly connected to said valve at said one time, and, configured for causing said sample container magazine advancement device to change which one of said plurality of sample containers is fluidly connected to said valve at said one time each time one of said plurality of sample containers in said sample container magazine has collected a sample of said de-icing fluid.

19. The system according to claim 9, said system further comprising
an information device for providing information relating to the circumstances of obtaining said sample of said de-icing fluid to said sampling control device, and
an information carrier for storing said information.

20. The system according to claim 19, wherein said information carrier is comprised by said sample container or said sample container magazine.

21. An airplane de-icer comprising a system according to claim 9.

22. The airplane de-icer according to claim 21, said airplane de-icer comprising a self-propelled vehicle provided with a lifting device for lifting and positioning a spraying nozzle in the vicinity of an outer surface of an airplane to be de-iced, said spraying nozzle being fluidly connected to a tank assembly via at least one pipe, wherein said tank assembly comprises separate tanks for an antifreeze fluid, such as propylene or ethylene glycol, additives, and water, each tank of the said assembly being fluidly connected to a mixing system via pipes, said mixing system being configured for mixing the fluids from each of said tanks into a de-icing fluid before supplying the de-icing fluid to the nozzle.

* * * * *